(12) United States Patent
Daley et al.

(10) Patent No.: US 8,867,192 B2
(45) Date of Patent: Oct. 21, 2014

(54) ELECTROLYTIC CAPACITOR INTERCONNECT

(75) Inventors: Jay E. Daley, Coon Rapids, MN (US); Eric Stemen, Roseville, MN (US); Steven E. Schultz, West Lakeland, MN (US); Daniel E. Then, Vadnais Heights, MN (US); Scott Zehrer, Ramsey, MN (US); Gregory J. Sherwood, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1450 days.

(21) Appl. No.: 12/495,352

(22) Filed: Jun. 30, 2009

(65) Prior Publication Data

US 2010/0010562 A1    Jan. 14, 2010

Related U.S. Application Data

(60) Provisional application No. 61/079,007, filed on Jul. 8, 2008.

(51) Int. Cl.
| | | |
|---|---|---|
| *H01G 9/00* | (2006.01) | |
| *H01G 9/008* | (2006.01) | |
| *H01G 9/10* | (2006.01) | |
| *A61N 1/375* | (2006.01) | |
| *H01G 9/14* | (2006.01) | |
| *A61N 1/39* | (2006.01) | |

(52) U.S. Cl.
CPC .............. *H01G 9/008* (2013.01); *A61N 1/3968* (2013.01); *H01G 9/10* (2013.01); *A61N 1/375* (2013.01); *H01G 9/14* (2013.01)
USPC .................. 361/523; 361/528; 607/5; 607/37

(58) Field of Classification Search
USPC ............. 607/36, 1, 5; 361/520, 522, 541, 538
See application file for complete search history.

(56) References Cited

U.S. PATENT DOCUMENTS

| | | | |
|---|---|---|---|
| 2004/0147960 A1* | 7/2004 | O'Phelan et al. ................ 607/1 |
| 2007/0097600 A1* | 5/2007 | Barr et al. ..................... 361/520 |
| 2007/0159768 A1* | 7/2007 | Sherwood et al. ............ 361/434 |
| 2007/0162077 A1* | 7/2007 | Sherwood ......................... 607/5 |

* cited by examiner

*Primary Examiner* — Kennedy Schaetzle
*Assistant Examiner* — Erica Lee
(74) *Attorney, Agent, or Firm* — Schwegman Lundberg & Woessner, P.A.

(57) ABSTRACT

An electrolytic capacitor is constructed as a stacked structure of alternating anode and cathode plates. A clip is fitted over a peripheral portion of each cathode plate, the clips being welded together to electrically connect the cathode plates in common. The dimensions of the clips are such that the clips take up approximately the same space away from the edges of the cathode plates as the thickness of the anode plate on each side of a cathode plate when the anode and cathode plates are stacked upon one another.

8 Claims, 4 Drawing Sheets

ELECTROLYTIC CAPACITOR INTERCONNECT

CROSS-REFERENCE TO RELATED APPLICATIONS

This application claims the benefit of U.S. Provisional Application No. 61/079,007, filed on Jul. 8, 2008, under 35 U.S.C. §119(e), which is hereby incorporated by reference.

FIELD OF THE INVENTION

This invention relates to capacitors and methods for their construction. In particular, the invention pertains to capacitors used in implantable cardiac rhythm management devices such as cardioverter/defibrillators and pacemakers.

BACKGROUND

Implantable cardiac rhythm management devices, including pacemakers and implantable cardioverter/defibrillators (ICDs), are devices used to treat abnormalities of heart rhythm. Pacemakers, for example, treat bradycardia (i.e., a heart rate that is too slow) by delivering pacing pulses to the heart at appropriate times, while ICDs terminate fibrillation by delivering a defibrillation shock pulse to the heart. Such devices containing pulse generating circuitry for delivering pacing or shock pulses that is enclosed by a housing and connected by leads to electrodes disposed in or near the heart. Many cardiac rhythm management devices incorporate both ICD and pacemaker functionality in the same device.

Most cardiac rhythm management devices use a capacitive discharge circuit to deliver either pacing or shock pulses to the heart. Owing to their high energy density and ability to withstand high voltages, electrolytic capacitors are used in these devices. An electrolytic capacitor is a layered structure that includes a metal anode plate with an insulating oxide layer formed on its surface for constituting a dielectric, a metal cathode plate, and an electrolyte impregnated in a separator between the two plates. The metal used for the anode and cathode plates is usually aluminum or tantalum. A capacitor is thereby formed from the capacitance between the negatively charged electrolyte and the positively charged anode plate with the oxide layer acting as a dielectric. A stacked-type electrolytic capacitor generally includes a stack of flat capacitive elements, with each element including a paper separator between two sheets of aluminum, one serving as an anode plate and the other as a cathode plate. In a stacked-type of aluminum electrolytic capacitor, anode and cathode plates (also referred to as coupons) are cut from aluminum sheets in a shape designed to conform to a capacitor case. The capacitive elements are connected together in parallel to provide a total capacitance.

DETAILED DESCRIPTION

Figure 1:
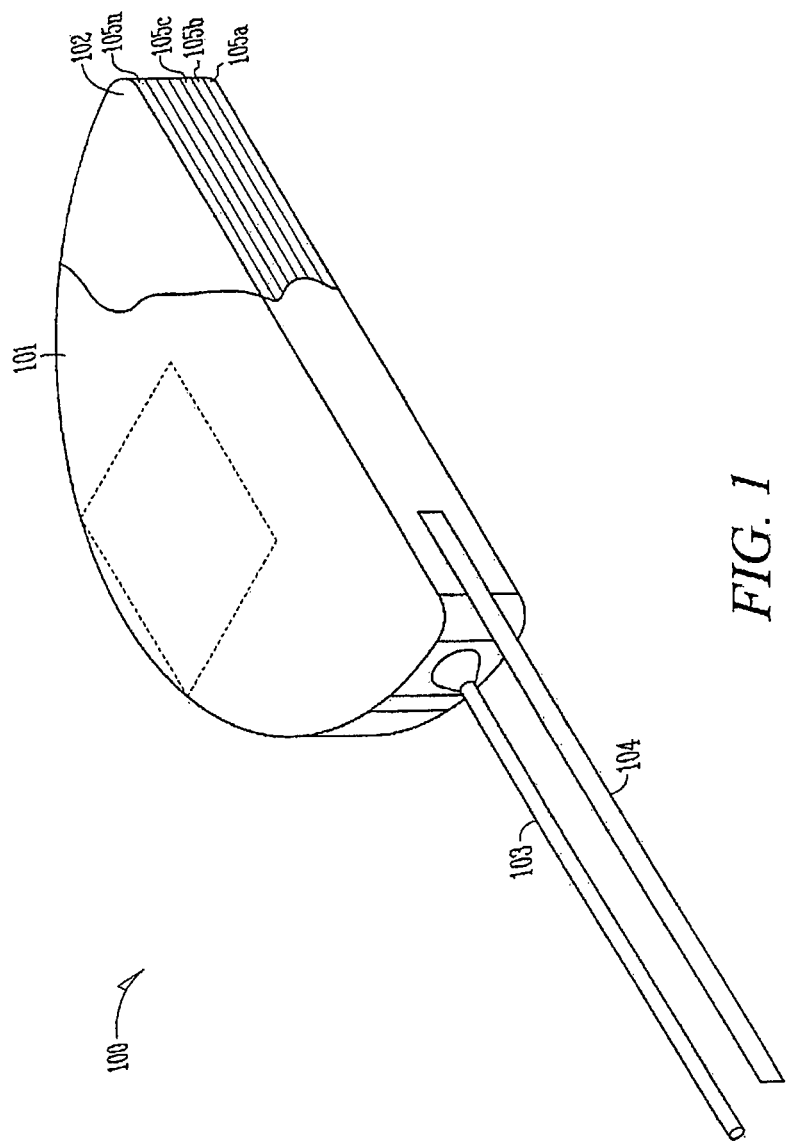
FIG. 1 shows an exemplary physical configuration of an electrolytic capacitor.

FIG. 1 illustrates an isometric view of a flat stacked-type capacitor 100, according to various embodiments. Although capacitor 100 is a D-shaped capacitor, in other embodiments, the capacitor is any other desirable shape. Capacitor 100 includes a case 101 which contains a capacitor stack 102. In the exemplary embodiment, case 101 is manufactured from a conductive material, such as aluminum, or a nonconductive material, such as a ceramic or a plastic. Capacitor 100 includes a first terminal 103 and a second terminal 104 for connecting capacitor stack 102 to an outside electrical component, such as heart monitor circuitry, cardioverter/defibrillator circuitry, or pacemaker circuitry. In the exemplary embodiment, terminal 103 is a feedthrough terminal insulated from case 101, while terminal 104 is directly connected to case 101. Capacitor stack 102 includes capacitor elements 105a, 105b, 105c through 105n, with each capacitor element 105a-105n including one or more cathodes, anodes, and separators. Each cathode is a foil structure and can include aluminum, tantalum, hafnium, niobium, titanium, zirconium, and combinations of these metals. In one embodiment, each cathode of capacitor stack 102 is connected to the other cathodes by welding or other connection methods which will be discussed below. The cathodes are coupled to conductive case 101, and terminal 104 is attached to case 101 to provide a cathode connection to outside circuitry. In other embodiments, the cathode is coupled to a feedthrough conductor extending through a feedthrough hole. The separator is located between each anode and cathode. In one embodiment, the separator includes one or more sheets of paper impregnated with an electrolyte. The electrolyte can be any suitable electrolyte for an electrolytic capacitor, such as an ethylene-glycol base combined with polyphosphates, ammonium pentaborate, and/or an adipic acid solute. In one embodiment, one or more of the anodes of capacitor stack 102 is a multi-anode stack which includes one, two, three or more anode foils having a variety of anode shapes. The anode foils are generally foil structures and can include aluminum, tantalum, hafnium, niobium, titanium, zirconium, and combinations of these metals. In one embodiment, at least portions of a major surface of each anode foil is roughened or etched to increase its effective surface area. This increases the capacitive effect of the foil with no relative increase in volume. Other embodiments incorporate other foil compositions and/or classes of foil compositions. In one embodiment, each anode is connected to the other anodes of the capacitor and coupled to feedthrough assembly 103 for electrically connecting the anode to circuitry outside the case. In some embodiments, the anodes are connected to the case and the cathodes are coupled to a feedthrough assembly. In other embodiments, both the anode and the cathode are connected to feedthroughs.

Figure 2:
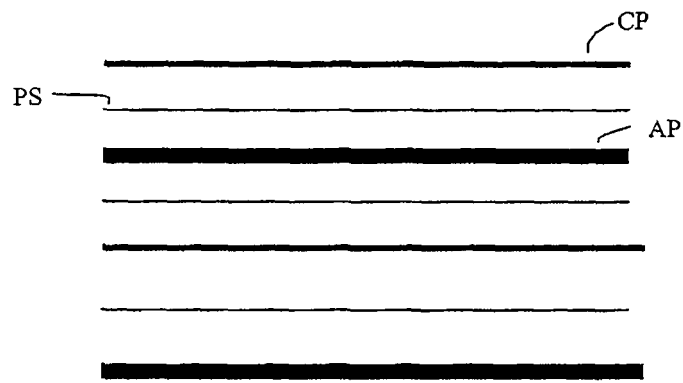
FIG. 2 shows a cross-sectional schematic of an electrolytic capacitor in a stacked configuration.

FIG. 2 shows a cross-sectional schematic of an electrolytic capacitor in a stacked configuration. The capacitor is made up of a plurality of capacitive elements that are stacked on one another and contained within a housing, with each capacitive element being a layered structure capacitor as described above. The anode plates AP are stacked on the cathode plates CP in alternate fashion with a paper separator PS interposed between each anode plate and each cathode plate. The paper separators are impregnated with a liquid electrolyte that allows current flow between the anode and cathode plates.

The anode plates have oxide layers formed on both sides so that each side of the anode plate together with the adjacent electrolyte constitutes a capacitive element. The cathode plates are electrically connected in common to a negative terminal, while the anode plates are electrically connected in common to a positive terminal. The individual capacitive elements of the capacitor are thus connected in parallel to give a total capacitance.

The anode plates may be constructed with unoxidized portions that may be welded together to make the electrical connections between the anode plates of the capacitor. The cathode plates, however, are much thinner than the anode plates, and this makes it problematic to directly weld the cathode plates together. For this reason, a metallic clip may be attached to the periphery of each cathode plate (e.g., by crimping or staking). The dimensions of the clips are such that they are flush against one another or nearly so when the capacitive elements are stacked upon one another. That is, the dimensions of the clips are such that the clips take up approximately the same space away from the edges of the cathode plates as the thickness of the anode plate on each side of a cathode plate when the anode and cathode plates are stacked upon one another. The clips may then be welded together to electrically connect the cathode plates. Utilizing a clip onto-cathode method increases the capacitor's reliability as it allows the assembly to be built without an anode-to-cathode cleave process which may introduce foreign material into the capacitor stack sub-assembly. In addition to foreign material reduction, the assembly benefits from the clips in that they provide a mass large enough to permit sufficient heat dissipation during the welding process which aides in preventing the cathode coupon from vaporizing and provides greater mechanical strength to the cathode interconnect area.

Figure 3:
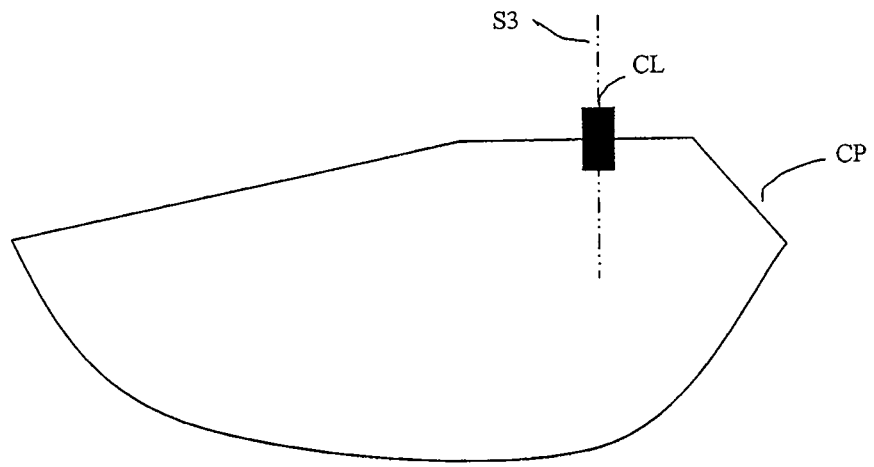
FIG. 3 is a top view of a capacitor stack showing an exemplary cathode plate with clip.
Figure 6:
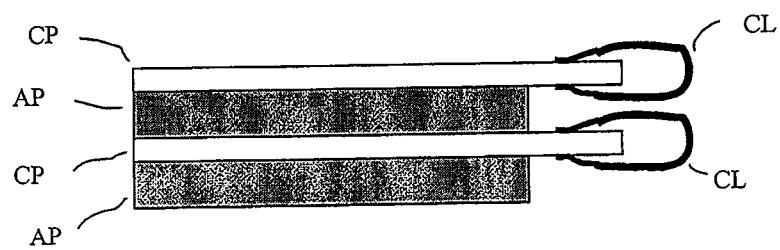
FIG. 6 shows a sectional view of the cathode and anode plates and attached clips.

In one embodiment, the clip is a section of aluminum ribbon wire that is attached to the cathode coupons by crimping it onto the coupon's edge. The thickness of the ribbon wire serves as a spacer roughly equal to the thickness of the anode coupon or group of anode coupons that are present on each side of a cathode coupon in a flat aluminum electrolytic capacitor. FIG. 3 is a top view of a capacitor stack showing an exemplary cathode plate CP according to one embodiment. The shape of the cathode plate is dictated by the shape of housing in which the stacked capacitive elements are to be contained. In order to electrically connect the plurality of cathode plates in the stack to one another, a metallic clip or tab CL is shown as being attached to the edge of the cathode plate CP. The clip CL fits over the edge of the cathode plate CP and may be attached thereto by staking or crimping. After the plurality of capacitive elements are stacked, the corresponding plurality of clips CL may then be welded together and connected to a terminal in order to establish the parallel connection. FIG. 6 shows a sectional view of the clips CL, cathode plates CP, and anode plates (the paper separators not being shown) of two capacitive elements along the line labeled S3 in FIG. 3. When the elements are stacked on one another, the two adjacent U-shaped clips CL have a thickness that takes up approximately the space same as the thickness of the anode plate on each side of the cathode plate to facilitate welding the clips together.

A problem that arises with electrolytic capacitors is the occurrence of an arc event in one of the capacitive elements (i.e., in one of the anode-cathode cells of the stack). Such an arc event may create a short circuit within the particular capacitive element that, since all of the capacitive elements are connected in parallel, prevents the capacitor from reaching its rated voltage and prevents the damaged capacitive element from being reformed. It is therefore desirable for an electrolytic capacitor to have a built-in fuse for each anode-cathode cell that makes up the capacitor. When an arc event occurs, all the stored energy of the capacitor contains is sent through the single cathode layer that contained the arc event (instead of being distributed among all of the cathode interconnections as during a normal discharge). If each cathode were to have a built-in fuse that open circuits when the current reaches a certain level in the interconnection path between the cathode plates, however, an arc event in one of the anode-cathode cells would fuse that cathode open and isolate the damaged section of the capacitor. The remaining portion of the capacitor would then be able to charge and discharge normally, although at a reduced energy level.

Figure 4:
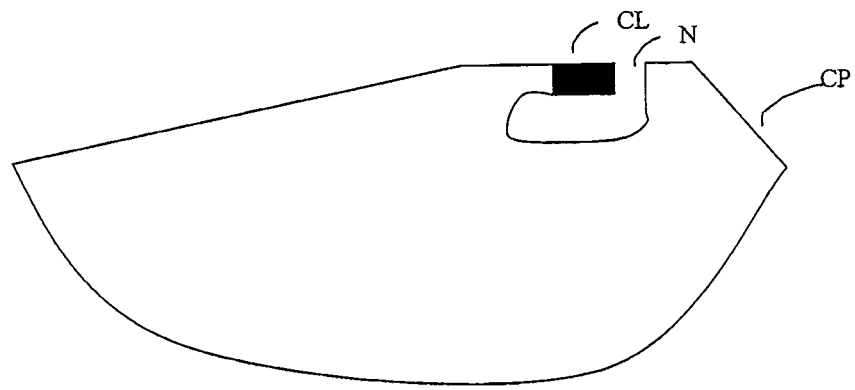
FIG. 4 is a top view of a capacitor stack showing an exemplary cathode plate with clip.
Figure 5:
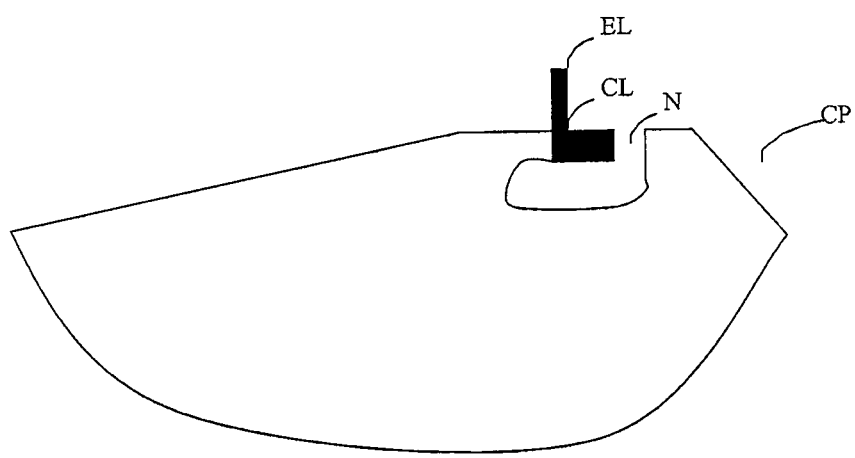
FIG. 5 is a top view of a capacitor stack showing an exemplary cathode plate with a clip having an additional connection leg.

FIGS. 4 and 5 illustrate cathode plates CP that are constructed in a manner to provide a fusing capability and obtain the advantages described above. The cathode plate CP in these embodiments has a notch at its periphery within which is an extending leg L of the cathode plate over which the clip CL is fitted in order to reduce the area of the cathode plate through which current is conducted to reach the clip and form a fusable link. In these embodiments, the notch N is an L-shaped notch that leaves a peripheral portion of the cathode plate as the extending leg. By reducing an area of the conduction path in the cathode plate through which current flows to the clip, the current density in that area may be increased to such an extent that the area will open circuit if a certain current amplitude is exceeded. For example, a dimension of the extending leg of the cathode plate within the notch is selected so that the fusable link open circuits at approximately 30 amps. In a particular embodiment, the anode and cathode plates are made of aluminum, the cathode plates are approximately 1 mil thick, and the extending legs are rectangular in shape with a width less than 60 mils.

FIG. 4 illustrates a top view of a capacitor stack with a cathode plate CP that has a notch N at its periphery within which is an extending leg L of the cathode plate over which the clip CL is fitted. In this embodiment, the notch N is an L-shaped notch that leaves a peripheral portion of the cathode plate as the extending leg. The sectional view through the clip and stacked cathode and anode plates shown in FIG. 6 corresponds to a view along the line labeled S4 in this embodiment.

FIG. 5 illustrates another embodiment showing cathode plate CP that has a notch N at its periphery within which is an extending leg L of the cathode plate over which the clip CL is fitted similar to that of FIG. 4. In this embodiment, one (or more) of the clips CL is L-shaped and has an extending leg EL for electrically connecting all of the cathode plates in the stack to the housing or other terminal. The sectional view through the clip and stacked cathode and anode plates shown in FIG. 6 corresponds to a view along the line labeled S5 in this embodiment.

Figure 7:
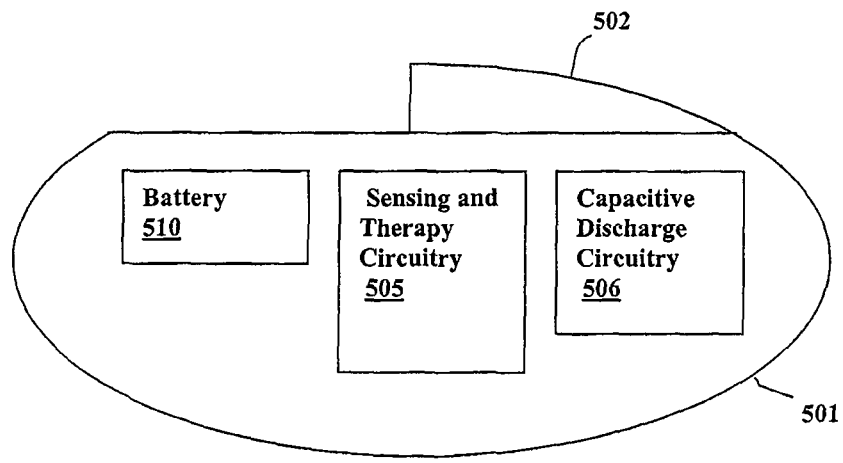
FIG. 7 depicts the layout of an implantable cardiac rhythm management device.

FIG. 7 shows a typical layout of an implantable cardiac rhythm management device. The housing 501 is usually made of titanium or other biocompatible metal and contains the electronic components necessary for sensing cardiac activity and delivering electrostimulation to the heart. These components include sensing and therapy circuitry 505, a capacitive discharge circuit 506 that include one or more electrolytic capacitors constructed as described above, and a battery 510. One or more leads with electrodes for disposition near the heart are connected to the sensing and therapy circuitry contained within the housing by means of a header 502 which has feedthroughs located therein for routing the leads to the appropriate internal components.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. An electrolytic capacitor, comprising:
a plurality of planar metallic anode plates with an insulating oxide layer formed on both surfaces of each anode plate for constituting a dielectric;
a plurality of electrolyte impregnated separators;
a plurality of planar metallic cathode plates;
wherein the capacitor is constructed as a stacked structure of alternating anode and cathode plates with an electrolyte impregnated separator interposed between each anode and cathode plate;
a clip fitted over a peripheral portion of each cathode plate, wherein the clip is attached to upper and lower surfaces of the peripheral portion of the cathode plate with a non-welded connection;
wherein the clips are welded together to electrically connect the cathode plates in common; and,
wherein the dimensions of the clips are such that adjacent clips are flush with one another when the anode and cathode plates are stacked upon one another.

2. The capacitor of claim 1 wherein each cathode plate has a notch thereby creating an extending leg at the peripheral portion of the cathode plate over which each clip is fitted.

3. The capacitor of claim 2 wherein the notch of each cathode plate is an L-shaped notch that leaves the peripheral portion of the cathode plate as the extending leg.

4. The capacitor of claim 1 wherein the clips are attached to the upper and lower surfaces of the peripheral portion of each of the cathode plates by crimping.

5. The capacitor of claim 1 wherein at least one of the clips has an extending leg for electrically connecting the cathode plates to a housing or other terminal.

6. The capacitor of claim 1 wherein the clips are comprised of a section of aluminum ribbon wire.

7. The capacitor of claim 1 wherein the clips are U-shaped.

8. The capacitor of claim 1 wherein the peripheral portion of each cathode plate, over which the clip is fitted, is an extended leg that is reduced in area to form a fusable link between the clip and the cathode plate.

* * * * *